United States Patent [19]

Abplanalp

[11] Patent Number: 4,931,402
[45] Date of Patent: Jun. 5, 1990

[54] PHOTOMETRIC ANALYSIS EQUIPMENT
[75] Inventor: Heinz Abplanalp, Hombrechtikon, Switzerland
[73] Assignee: Tecan AG Analytische Instrumente, Hombrechtikon, Switzerland
[21] Appl. No.: 127,291
[22] PCT Filed: Feb. 27, 1987
[86] PCT No.: PCT/CH87/00022
 § 371 Date: Oct. 29, 1987
 § 102(e) Date: Oct. 29, 1987
[87] PCT Pub. No.: WO87/05401
 PCT Pub. Date: Sep. 11, 1987

[30] Foreign Application Priority Data
 Mar. 6, 1986 [CH] Switzerland ............. 00924/86
[51] Int. Cl.$^5$ ............................. C12M 1/34
[52] U.S. Cl. .............................. 435/291; 435/292; 356/244; 422/63
[58] Field of Search ............ 435/288, 291, 287, 292; 356/419, 73, 416, 39, 72, 244, 246; 422/63, 65, 67, 68, 75

[56] References Cited
U.S. PATENT DOCUMENTS 3,687,632  8/1972  Natelson .
4,322,216  3/1982  Lillig et al. .
4,584,275  4/1986  Okano et al. ............ 435/291 X
4,613,573  9/1986  Shibayama et al. ......... 356/244 X
4,678,752  7/1987  Thorne et al. ............ 435/291
4,724,215  2/1988  Farber et al. ............ 435/291
4,785,407  11/1988 Sakagami ................ 356/246 X FOREIGN PATENT DOCUMENTS
25350  3/1981  European Pat. Off. .
46430  2/1982  France .

Primary Examiner—Larry Jones
Attorney, Agent, or Firm—Walter C. Farley

[57] ABSTRACT

A photometric analyzer includes a primary rack (1) for holding a number of sample tubes (2), and a work table (3) located alongside the primary rack (1) for supporting a microtitration plate (4), the work table being positionable in any x/y direction desired in a horizontal plane. A sample distribution arm (5) is located above the primary rack (1) and the work table and can be positioned in any x/y direction in the horizontal plane. A photometer (6) is located in the positioning sector of the work table (3) whose beam path (7) vertically intersects the x/y plane of the work table (3). A programmable computer (8) is provided for controlling the entire photometric analysis equipment. The device is particularly suitable for performing enzyme immune tests.

7 Claims, 1 Drawing Sheet

PHOTOMETRIC ANALYSIS EQUIPMENT

The invention relates to a photometric analyzer which serves to determine the end point of chemical reactions, for example of enzyme immune tests (EIA, enzyme immunoassay, or ELISA, enzyme-linked immuno-sorbent assay).

BACKGROUND OF THE INVENTION

The previously known photometric analyzers are complicated in the way they perform the analysis, susceptible to error because of the lack of complete automation of the system, and not multifaceted because the individual analysis steps are inflexibly connected to each other.

DE-A1-3500639, for example, describes a photometric analyzer which has a fixed sample release device, a separate reagent release device that is also fixed, a number of photometers that operate parallel to the horizontal plane, a computer which calculates only the photometric values as well as a separate control device for the various mechanical motion and release devices.

This known apparatus is difficult to operate and cannot be adapted to changing analysis procedures and requirements. The lack of computerized monitoring of the entire system and the many separate operating components increase the susceptibility of this equipment to make errors and to break down.

SUMMARY OF THE INVENTION

The invention provides a remedy for some of these shortcomings. The invention, as is characterized in the claims, provides a photometric analyzer which allows for absolutely controlled analysis processing from the preparation of the samples to the assessment of the results of the photometric measurements and which guarantees the highest degrees of reliability and flexibility as a result of its simple design and an optimal connection of the different components.

The advantages achieved by the invention can essentially be seen in the fact that the analysis equipment is compact and multifaceted and can operate practically error-free because it is virtually fully automatic and because of the controls of the movement processes.

BRIEF DESCRIPTION OF THE DRAWING

The drawing shows a perspective schematic view of an analyzer apparatus in accordance with the invention.

DESCRIPTION OF THE PREFERRED EMBODIMENTS

Figure 1:
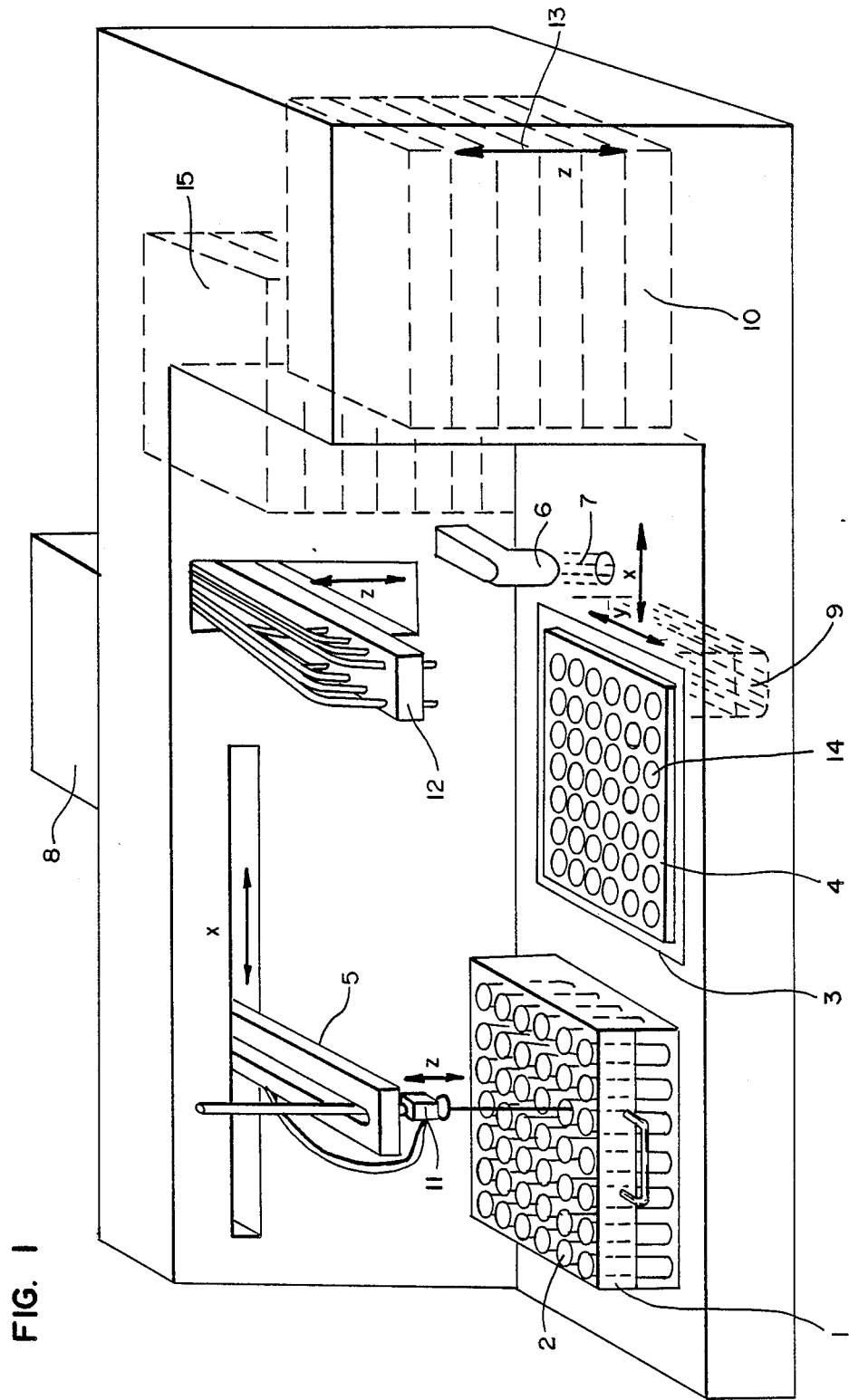

The analysis equipment presented by the invention and its method of operation is described below in detail with the aid of some examples. The samples selected for analysis, for example the reagents required for an enzyme immune test (EIA or ELISA), and the test fluids to be examined are situated on a primary rack 1 in positions assigned according to the computer program. The primary rack 1 is placed at the designated position of the analysis equipment and the computerized automatic machinery is set into operation. The analyzer then removes the amounts of test fluids and reagents necessary for analysis by means of the single channel pipette 11 supported on the sample distribution arm 5 and thereby conveys these materials to the microtitration plate 4 located on the designated point of the work table 3.

The microtitration plate 4 that has been prepared in such a fashion is then moved into the incubator 10, located on the work table 3, which can be moved in any desired x or y direction in the horizontal plane. The role of the incubator 10 is to store the liquids located on the microtitration plate 4 at an increased temperature (25°–37° C.) in order, for example, to coat the microtitration plate 4 with antigens or antibodies. Because the incubation period typically is between 30 and 120 minutes, a lift 13 is provided in the incubator which allows for the vertical storage of up to six microtitration plates 4. Following successful incubation, the microtitration plate 4 is again removed from the incubator 10 and returned to its original position on the work table 3 and is rinsed by means of the four-way peristaltic pump having the multiple head 12 (double four-way head whose eight nozzles have one tube each to the peristaltic pump). The rinsing fluid drains into the rinse trough 9. The coating with antigens or antibodies that remains on the microtitration plate 4 is displaced by means of the four-way peristalsis of the reagent release part of the multiple head 12 with the required amount of reagent and the microtitration plate is again returned to the incubator 10. This procedure (cleaning/addition of reagent/incubation) can be repeated several times, depending upon the test being performed.

The color reaction, for example catalyzed by a peroxidase enzyme, which is necessary for the subsequent photometric measurement, occurs in this last step. The color reaction can be halted either by adding a suitable solution or be measured directly after a programmed reaction interval.

The microtitration plate 4 is then passed through the beam path 7 of the photometer 6 located on the work table. At this point, the photometric measurement of the individual colored solutions that are located in recesses 14 of the microtitration plate 4 can take place. The wave lengths used are typically between 340 to 700 nm, wherein it is preferred to operate bichromatically with a filter photometer (eight different wave lengths).

The use of microtitration plates 4, designed as flat base plates, has proven to be especially expedient because no deviation of the beam path, which could distort the photometric measurement as in the case of round base plates, can occur.

Once the photometric measurement has been taken, the microtitration plate 4 can be removed manually from the work table 3 and discarded.

Furthermore, all work steps are performed automatically and are monitored by a programmable computer 8. The analyzer itself is essentially controlled by a separate computer, for example by an IBM PC, whereas a computer integrated into the analysis equipment serves only to distribute the commands to the different subcomponents, as well as for its monitoring.

Another improved embodiment of the analysis equipment presented by the invention consists of designing the primary rack 1 in the form of a rotating plate and of designing the analysis equipment itself with a coded line reader. As a result, the reliability of the analysis can be further increased because the possibility of a mistaken substitution of the samples is virtually excluded.

The capacity and flexibility of the photometric analyzer presented by the invention can also be increased further by providing for a storage station 15 for microtitration plates 4 in the inflow section of the work table 3. The storage station is preferably provided with a lifting mechanism and allows for the storage of fresh or already processed microtitration plates 4.

What is claimed is:

1. Photometric analyzer, in particular for performing enzyme immune tests, characterized by a primary rack for holding a variety of sample tubes;
   a work table located alongside the primary rack for supporting a microtitration plate 4 wherein the work table can be positioned in any x/y direction desired in a horizontal plane;
   a sample distribution arm which is located above the primary rack and the work table and which can be positioned in any x/y direction in a horizontal plane;
   a photometer fixedly located in the positioning sector of the work table whose beam path vertically intersects the x/y plane of the work table; and
   a programmable computer for controlling the entire photometric analysis equipment.

2. Photometric analyzer in accordance with claim 1 characterized by a multiple head with a suction and/or reagent release function which is located above the work table and can move in the vertical direction z.

3. Photometric analyzer in accordance with claim 2 characterized by an incubator for holding one or more microtitration plates and having a lift mechanism.

4. Photometric analyzer in accordance with claim 3 characterized by the fact that the sample distribution arm bears a single channel pipette which can be moved in the vertical direction.

5. Photometric analyzer in accordance with claim 4 characterized by the fact that the multiple head, which preferably is designed as a double four-way head, has a four-way peristalsis for reagent release and/or a four-way peristalsis for suction.

6. Photometric analyzer in accordance with claim 5 characterized by the fact that the microtitration plate is designed as a flat base plate.

7. Photometric analyzer in accordance with claim 6 characterized by having a rinse fluid trough located below the path of the work table.

* * * * *